United States Patent
Sakakita et al.

(10) Patent No.: US 9,713,242 B2
(45) Date of Patent: Jul. 18, 2017

(54) PLASMA TREATMENT EQUIPMENT

(75) Inventors: Hajime Sakakita, Tsukuba (JP); Yuzuru Ikehara, Tsukuba (JP); Satoru Kiyama, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 13/808,168

(22) PCT Filed: Jun. 27, 2011

(86) PCT No.: PCT/JP2011/064661
§ 371 (c)(1),
(2), (4) Date: Mar. 25, 2013

(87) PCT Pub. No.: WO2012/005132
PCT Pub. Date: Jan. 12, 2012

(65) Prior Publication Data
US 2013/0204244 A1    Aug. 8, 2013

(30) Foreign Application Priority Data
Jul. 7, 2010    (JP) .................. 2010-154948

(51) Int. Cl.
*A61B 18/04*    (2006.01)
*H05H 1/24*    (2006.01)
*A61B 18/00*    (2006.01)

(52) U.S. Cl.
CPC ............. *H05H 1/24* (2013.01); *A61B 18/042* (2013.01); *H05H 1/2406* (2013.01); *A61B 2018/00589* (2013.01); *A61B 2018/00982* (2013.01); *H05H 2001/245* (2013.01); *H05H 2001/2412* (2013.01)

(58) Field of Classification Search
CPC .................... A61B 2018/00583; A61B 18/042
USPC ................ 606/27, 28, 32, 34, 40, 41, 45, 49
See application file for complete search history.

(56) References Cited

U.S. PATENT DOCUMENTS

3,903,891 A * 9/1975 Brayshaw ........................ 606/27
6,723,091 B2 * 4/2004 Goble et al. .................... 606/41
(Continued)

*Primary Examiner* — Ronald Hupczey, Jr.
*Assistant Examiner* — Bo Ouyang
(74) *Attorney, Agent, or Firm* — Wenderoth, Lind & Ponack, L.L.P.

(57) ABSTRACT

A plasma treatment equipment includes: a plasma starting and stabilizing unit (A) having an insulating material such as a dielectric material having an elongated hole connecting to a plasma ejection portion, a triggering and discharge-stabilizing electrode, and an intense electric field electrode mounted thereon; and a plasma generating unit (B) including the insulating material having the elongated hole and a plasma generating electrode configured to perform main plasma generation at the time of operation, wherein the triggering and discharge-stabilizing electrode, the intense electric field electrode, and the plasma generating electrode are provided in such a manner that all the electrodes are not exposed and covered with the dielectric material for the entire space of one or more of the elongated hole which allows passage of gas from the upstream, starting of the plasma and generation of the plasma, and ejection of the plasma jet.

13 Claims, 4 Drawing Sheets

(56) References Cited

U.S. PATENT DOCUMENTS

| | | | |
|---|---|---|---|
| 6,958,063 B1* | 10/2005 | Soll | A61B 18/042 |
| | | | 606/32 |
| 7,271,363 B2* | 9/2007 | Lee et al. | 219/121.43 |
| 7,387,625 B2* | 6/2008 | Hovda et al. | 606/32 |
| 8,123,744 B2* | 2/2012 | Podhajsky | 606/41 |
| 8,182,480 B2* | 5/2012 | Huseman | 606/49 |
| 8,994,270 B2* | 3/2015 | Koo et al. | 315/111.21 |
| 2005/0285476 A1* | 12/2005 | Chou et al. | 310/317 |
| 2008/0262488 A1* | 10/2008 | Penny et al. | 606/28 |
| 2009/0069807 A1* | 3/2009 | Eggers et al. | 606/48 |
| 2010/0100091 A1* | 4/2010 | Truckai | 606/33 |
| 2010/0125267 A1* | 5/2010 | Lee et al. | 606/27 |

\* cited by examiner

PLASMA TREATMENT EQUIPMENT

TECHNICAL FIELD

The present invention relates to plasma treatment equipment.

BACKGROUND ART

In recent years, aiming to treat various materials, or for medical applications or the like, studies related to the use of plasma generated by devices on the basis of various discharging principles under an atmospheric pressure environment have been conducted.

Non-Patent Document 1 discloses a conventional arc-discharge type endoscope-mounted plasma device using an RF power source which was developed for medical use. However, this device is configured to pass an electric current to human bodies and hence trigger thermocoagulation caused by resistance heating, generate high energy, and hence may cause tissue damage depending on the usage. In addition, since a discharge path moves to an area having less electrical resistance, the device has various drawbacks in operability. Therefore, even though continuous treatment is intended for the purpose of reliable hemostasis, such continuous treatment is difficult due to an increase in electrical resistance caused by the thermocoagulation. Accordingly, there are problems in both aspects of safety for tissues of human bodies and operability in treatment work.

On the other hand, a conventional device using a dielectric-barrier discharge disclosed in Non-Patent Document 2 is subject to less heat load because it uses plasma at low temperatures (on the normal temperature level), and hence provides a hemostasis approach on the basis of a new coagulant effect principle other than heat, so that advantages such as reduction of load to living bodies are achieved. However, this device has a relatively large treatment surface, and hence there is a problem in operability. In addition, since a human body or an object to be treated serves as the grounding electrode and discharges electricity in the atmosphere, there is a problem in that the electric current tends to flow through the human body or the object to be treated, and a streamer discharge tends to occur. When the streamer discharge occurs, part of the human body or the object to be treated may be damaged.

Further, Patent Document 1 discloses a jet-blow type plasma device using dielectric-barrier discharge. This device is a device central to preparing material or performing surface modification. However, since the device has a structure in which a metallic electrode is exposed to the plasma and also faces a material, the material may discharge by itself depending on the conditions.

As another type, Patent Document 2 discloses a plasma treatment device used for cleaning of foreign substances such as organic substances existing on the surface of a treated substance such as an electronic component or surface modification. This device has an advantage in that glow discharge may be generated stably and uniformly. However, since this device has an internal electrode facing the treated substance, there is a problem in that the electric field intensity with respect to the treated substance is increased and hence an electric current becomes large, the delicately treated substance may be damaged.

Patent Document 3 discloses a plasma treatment equipment which is capable of generating a relatively homogeneous glow discharge and hence restrains generation of a streamer discharge, thereby being capable of reducing damage to the treated substance. However, since this device has an internal electrode covered with a dielectric material facing the treated substance, there is a case where the electric field intensity with respect to the treated substance is increased, and hence an electric current becomes large, so that the delicate treated substance may be damaged. In addition, a gas diffusion panel is mounted and hence there is a problem in that the size of the device is increased.

Patent Document 4 discloses a device configured to arrest bleeding used for the purpose of hemostasis. However, a high-temperature plasma of 4,500 K to 10,500 K or so is generated, and coagulation on the basis of heat is achieved. Therefore, there is a problem in that the surface tissue is carbonized and a necrotic layer is formed.

Patent Document 5 discloses a plasma knife having a configuration in which an electric field intensity with respect to a living body is further increased to enhance hemostasis characteristics for the device disclosed in Patent Document 4. However, because of a configuration in which the electric field intensity is enhanced, there is a problem in that the tissue damage may further be remarkable and serious.

Patent Document 6 discloses a hemostasis device using lower-temperature plasma utilizing microwaves for the purpose of hemostasis. However, according to this device, since the electrode is exposed in the vicinity of the living body and the discharge occurs outside, there is a risk of contact with tissue of the living body. In addition, the material may be damaged when treated therewith. Furthermore, the jet length is extremely short, with a length of 4 mm or so with a power of 5 watts and a flow rate of 2 slm, so there is a drawback in operability.

Patent Document 7 discloses a surgical device configured to generate plasma by an arc discharge between a pair of electrodes and eject plasmatized gas used for performing electrical surgical treatment. However, this device is subject to a high temperature at an electrode portion and there is a problem in durability or the like.

As described above, when discharge energy is high, there is a problem in that the delicate object or substance to be treated, such as in medical use, may be damaged due to the plasma treatment. Therefore, since only weakening energy makes the start of generation of plasma under the environment of the atmospheric pressure difficult, an electrode for generating plasma is provided in the vicinity of the ejection port or so as to be exposed for generating plasma in the prior art. In addition, in the prior art, even though the plasma having weakened energy as described above can be generated once under the environment of the atmospheric pressure, dangerous phenomena such that the treatment conditions change because the plasma is unstable, or the object to be treated may be damaged by the streamer discharge or the like, tend to occur, so that treatment in medical use or the like has been almost impossible. In this manner, low-energy plasma treatment equipment under the environment of atmospheric pressure which allows plasma treatment in the medical field and plasma treatment in an industrial field is strongly expected.

PRIOR ART DOCUMENTS

Patent Documents

Patent Document 1: International Publication WO2005/125286
Patent Document 2: JP-A-2000-282243
Patent Document 3: Japanese Patent Application No. 2009-144262

Patent Document 4: International Publication WO 96/06572
Patent Document 5: International Publication WO99/66852
Patent Document 6: Patent Application No. 2009-154819
Patent Document 7: JP-A-10-234744

Non-Patent Documents

Non-Patent Document 1: K. E. Grund, et al., Endoscope Surgery 2 (1994) 42,
Non-Patent Document 2: Sameer U. Kalghatgi, et al., IEEE Transactions on Plasma Science 35, No. 5 (2007) 1559-1565.

SUMMARY OF THE INVENTION

Problems to be Solved by the Invention

Accordingly, a problem to be solved by the present invention is to provide medical and non-medical plasma treatment equipment to be used in the industrial field, agricultural field, livestock industry field, forest industry field, fisheries industry, and the like. The equipment should be free from a risk of occurrence of discharge on an object to be treated from an electrode for generating plasma when starting a mild plasma treatment and which does not cause a temperature increase more than necessary. The equipment should be capable of performing the start of the plasma generation easily and reliably and once generated the state of the mild plasma jet should be stably maintained without fluctuations, the length thereof should be formed into a shape having a length of approximately 10 mm or longer, and a diameter of approximately 1 mm or smaller. In plasma treatment using a mild plasma jet, it should be a compact, light-weight, and easy-to-control configuration with superior, operability and capable of fine spot treatment on an object.

Means for Solving the Problems

In order to solve the above-described problem, a plasma treatment equipment according to the present invention is a plasma treatment equipment including: a plasma starting and stabilizing unit (A) having an insulating material such as a dielectric material having one or more elongated holes connecting to a plasma ejection portion, a triggering and discharge-stabilizing electrode, and an intense electric field electrode mounted thereon; and a plasma generating unit (B) including the insulating material having the elongated hole and a plasma generating electrode configured to perform main plasma generation at the time of operation, wherein the triggering and discharge-stabilizing electrode, the intense electric field electrode, and the plasma generating electrode are provided in such a manner that all the electrodes are not exposed, and covered with the dielectric material for the entire space of one or more of the elongated holes which allow passage of gas from the upstream, starting of the plasma and generation of the plasma, and ejection of the plasma jet.

Also, for easy start of discharge, the plasma treatment equipment of the present invention is characterized in that the triggering and discharge-stabilizing electrode and the intense electric field electrode of the plasma starting and stabilizing unit (A) are provided at positions where electric field intensity is enhanced in the space where gas passes, and start discharge in order to allow easy start of discharge.

Also, the plasma treatment equipment of the present invention is characterized in that the intense electric field electrode of the plasma starting and stabilizing unit (A) and the plasma generating electrode of the plasma generating unit (B) are provided integrally or coupled, in order to continuously generate sufficient plasma efficiently after the start of discharge.

Also, the plasma treatment equipment of the present invention is characterized in that a high-frequency electric field shield member formed of a metallic material completely covered with an insulating material such as vinyl is provided on an outer surface of a dielectric material which constitutes the plasma ejection port, and the metallic material concerned is grounded via impedance or grounded directly for the purpose of resisting leakage of the high-frequency electric field from a distal end portion of the ejection port for the safety of an object to be treated.

Also, the plasma treatment equipment of the present invention is characterized in that an inner surface of one or more of the elongated hole for supplying gas is provided with concavity and convexity in order to allow easy start of discharge by varying the electric field distributed in the space of the elongated hole.

Also, the plasma treatment equipment of the present invention is characterized in that a dielectric cover as an insulating material is provided in order to increase the insulation, so as to cover an outermost portion of the plasma treatment equipment for the safety of an operator who operates the plasma treatment equipment.

Also, the plasma treatment equipment of the present invention is characterized in that a metallic cover is provided so as to cover the dielectric cover which is the outermost portion of the plasma treatment equipment, and an air layer is provided between the dielectric cover concerned and the metallic cover concerned in order to further enhance the safety of the operator who operates the plasma treatment equipment.

Also, the plasma treatment equipment of the present invention is characterized in that the high-frequency electric field shield member mounted on a tip end portion as the plasma ejection port is provided by mounting on the metallic cover in the vicinity of the tip end portion of the ejection port, and the metal concerned is provided by connecting to the zero potential side of the power source output or being grounded for the safety of the object to be treated.

Also, the plasma treatment equipment of the present invention is characterized in that the metallic cover is covered with a sheet of an insulating material in order to enhance the safety of the operator who operates the plasma treatment equipment.

Also, the plasma treatment equipment of the present invention is characterized in that a high-voltage supply source is a high-frequency power source using a piezoelectric element in order to achieve a compact and a small capacitance.

Also, the plasma treatment equipment of the present invention has the plasma to be generated be intermittent plasma so as to be capable of controlling time average value of the energy of the mild plasma treatment and using intentional variations of the plasma jet on the other hand.

Also, the plasma treatment equipment of the present invention includes a pulse gas supply device configured to supply gas to be supplied in a pulsed manner for generation of intermittent jets of plasma.

Also, the plasma treatment equipment of the present invention includes an ejector for a blood coagulation booster or the like for enhancing hemostasis workability in the medical field.

Also, a plasma treatment method of the present invention treats an object with a plasma jet using the plasma treatment equipment described above.

Also, a plasma treatment method of the present invention treats an object applied with a blood coagulation booster or a material surface treatment agent is treated with plasma using the plasma treatment equipment described above.

Effect of the Invention

Since the plasma treatment equipment of the present invention has the configuration as described above, there is provided the medical and non-medical plasma treatment equipment to be used in industrial field, agricultural field, livestock industry field, forest industry field, fisheries industry, and the like, which is free from a risk of occurrence of discharge on the object to be treated from the electrode for generating plasma when starting the mild plasma treatment. The equipment does not cause a temperature increase more than necessary, is capable of performing the start of the plasma generation easily and reliably, and, once generated, the state of the plasma jet is stably maintained without fluctuations. The length thereof may be formed into a shape having a length of approximately 10 mm or longer, and a diameter of approximately 1 mm or smaller. In plasma treatment using a mild plasma jet, compact, light-weight, and easy-to-control configuration is achieved, operability is superior, and capable of fine spot treatment on the object.

BRIEF DESCRIPTION OF DRAWINGS

FIGS. 2(a), (b), and (c) are explanatory drawings illustrating respective cross sections taken along the lines AA', BB', CC' of Example 1 of the present invention.

BEST MODE FOR CARRYING OUT THE INVENTION

In order to solve the above problems, main configurations of plasma treatment equipment of the present invention are a plasma starting and stabilizing unit (A) and a plasma generating unit (B).

The plasma starting and stabilizing unit (A) is a device portion which facilitates and ensures plasma generation. Examples of such means include a configuration in which electric field intensity is enhanced between a triggering and discharge-stabilizing electrode and an intense electric field electrode. In other words, the configuration is such that an insulating material such as a dielectric material having one or more elongated holes for supplying gas and one or more holes for introducing triggering and discharge-stabilizing electrode includes an intense electric field electrode that supplies power to the outside of the insulating material attached thereto on the opposite side from the triggering and discharge-stabilizing electrode with respect to the elongated hole of supplying gas in close contact therewith, the triggering and discharge-stabilizing electrode and the intense electric field electrode are provided close to each other, and discharge of the introduced gas is started in a space in the elongated hole for supplying gas. The triggering and discharge-stabilizing electrode is used not only for starting discharge, but also has a role to avoid abnormal discharge at another area after the plasma generation by the plasma generating unit (B) and maintain the discharge stably.

On the other hand, the plasma generating unit (B) is a device portion configured to take over the plasma once generated by the plasma starting and stabilizing unit (A) and generate the plasma continuously. Examples of such means include a configuration in which plasma is generated in the space of the hole in the insulating material having the elongated hole by a plasma generating electrode attached to the outside of the insulating material having the elongated hole in closely attached manner.

By the combination of (A) and (B), the plasma is stably maintained, a plasma jet is generated stably without changing the shape and the length, and treatment conditions are stabilized without fluctuations, so that fine spot treatment is enabled. Further, this enables the realizations of plasma treatment equipment configured to allow a plasma jet to be ejected through an ejecting portion located on the opposite side from a gas inlet port.

A frequency of the voltage to be used is on the order of 1 kHz to 100 kHz and, in Examples described later, a frequency of approximately 60 kHz is used. A step-up transformer is not limited in type, but is characterized by employment of a system in which voltage is increased by mainly using a piezoelectric element. Gas used here is mainly inert gas. However, mixed gas mixed with inert gas of a different type, or mixed gas mixed with active gas may be used. The dielectric material as the insulating material has preferably a dielectric constant of approximately 100 or below, and quartz, silicon, alumina, zirconia, and the like are normally used. A diameter of a tip end portion of the nozzle is on the order of approximately 1 mm or so.

EXAMPLES

Example 1

The present invention will be described below in detail on the basis of Examples.

Figure 1:
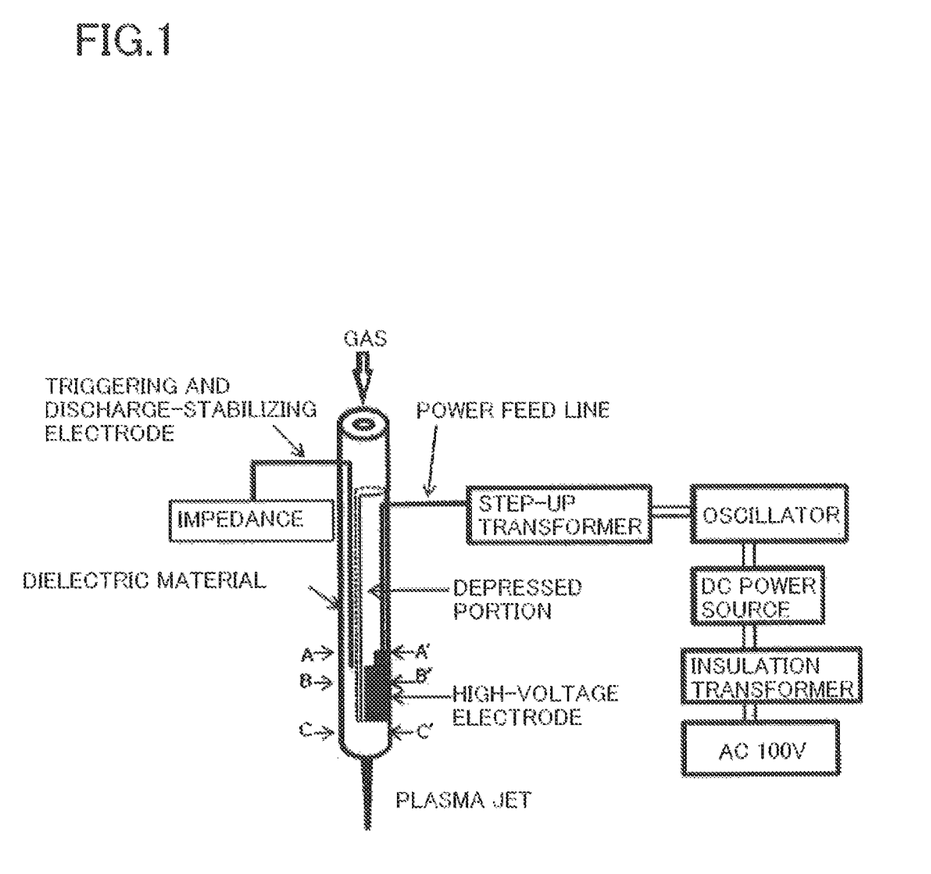
FIG. 1 is an explanatory drawing illustrating Example 1 of the present invention.

FIG. 1 is a drawing of Example 1 which is an example of the present invention. As illustrated in FIG. 1, a copper wire or the like as the triggering and discharge-stabilizing electrode is inserted into the dielectric material such as quartz. To the electrode, discharge is performed to a space via impedance (earth capacity or the like) or is grounded. A high-voltage electrode to which a voltage is applied is provided in a depressed portion having a depression deeper than the thickness of the high-voltage electrode on the dielectric material described above in close contact therewith from the outside. The frequency of AC voltage to be applied from a power source via a power feed line is, for example, 60 kHz, and peak-to-peak voltage of the applied voltage is on the order of 7.5 kV or so. In the drawing, a power source system is composed of a commercial power source, an insulation transformer, a DC power source, an oscillator, and a step-up transformer in this order. The power is supplied from the commercial power source via the insulation transformer to the DC power source. However, the DC power source may be replaced by a rechargeable battery. The zero-potential side of the DC power source output may be grounded. Gas, helium gas in this case, was introduced into the elongated hole for supplying gas at a flow rate of 2 L/min or so from a pipe for supplying gas, the introduced gas was discharged on the inner surface of the dielectric material of the high-voltage electrode portion to generate plasma, and a plasma jet was ejected from the ejection port. As illustrated in the drawing, the inner diameter of the tip end portion as the ejection port may be the same as the inner diameter of the elongated hole for supplying gas, or a nozzle having a small diameter and formed of a dielectric material may be mounted at the tip end portion thereof to cause the plasma to be ejected therefrom. The shorter distance is more preferable between the high-voltage electrode and the gas pipe, for example, such as 0.6 mm or so.

Figures 2A, 2B, 2C:
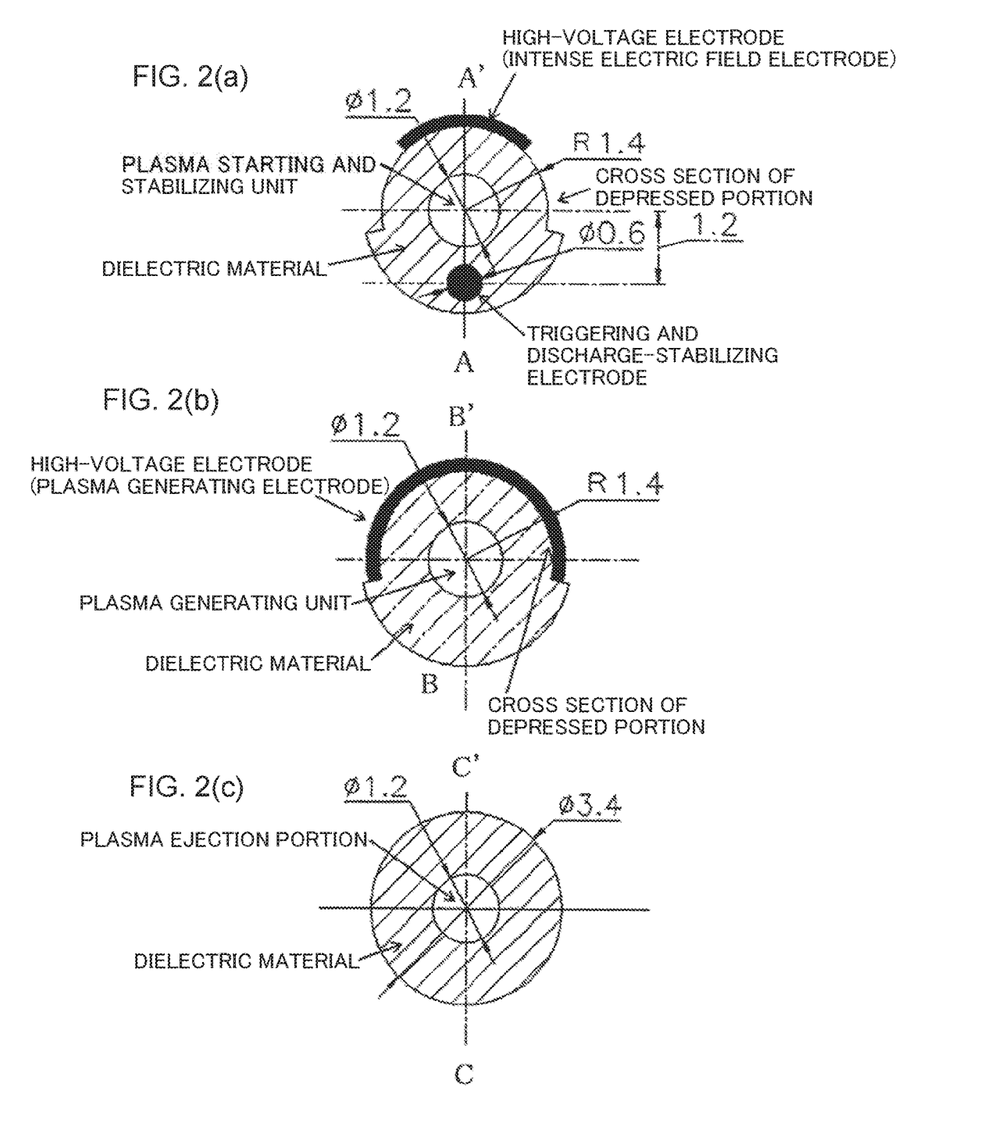

FIGS. 2(a), (b), and (c) illustrate respective cross sections (AA' plane, BB' plane, CC' plane) of the plasma treatment equipment of the present invention illustrated in FIG. 1. As described above, the AA' plane is a cross section of the plasma starting and stabilizing unit (A) and the BB' plane is a cross section of the plasma generating unit (B). Starting of the plasma is performed by the plasma starting and stabilizing unit (A). Discharge with an intense electric field is started in the space at the center of the AA' plane located between the triggering and discharge-stabilizing electrode and the intense electric field electrode. Although the triggering and discharge-stabilizing electrode and the intense electric field electrode are provided so as to face the elongated hole where gas passes in the drawing, they do not have to face each other as long as the arrangement contributes to enhance the intensity of the electric field.

The plasma starting and stabilizing unit (A) generates a plasma jet stably without changing the shape and the length thereof, and enables a fine spot treatment stably without fluctuations of treatment conditions. Continuously, in the mild plasma generating unit (B), the plasma continues to be generated in the space at the center of the BB' plane. A configuration in which the plasma proceeds from the space at the center of the BB' plane to a space on the CC' plane, so that a plasma jet is stably ejected from the ejection port, is thus achieved.

The hole at the center in FIG. 2 (a) is an elongated hole for supplying gas, and the triggering and discharge-stabilizing electrode is introduced into the hole on the lower side of the drawing. The intense electric field electrode and the plasma generating electrode may be formed into a square shape. However this Example is characterized in that the intense electric field electrode is smaller than a semicircle to enhance the electric field intensity, so that gas passes an area with more intensive electric field (FIG. 2(a)) and is also characterized in that the plasma generating electrode is larger than the intense electric field electrode in FIG. 2(a) to enlarge the surface area where the plasma is generated (FIG. 2(b)). The intense electric field electrode and the plasma generating electrode may have an integral structure or be connected by a cable, or may be provided separately.

Also, as illustrated in FIG. 2(c), the configuration is characterized in that the high-voltage electrode is hidden by the dielectric material when viewed from the upper and lower directions, so that discharge with respect to the outside hardly occurs. The larger the high-voltage electrode, the larger amount of generation of plasma is generated. Further, the inner wall of the elongated hole for supplying gas may be provided with concavity and convexity on the inner surface thereof for the purpose of facilitating generation of plasma by varying the intensity of the local electric field when viewed from respective cross sections of AA' plane, BB' plane, and CC' plane.

Since Example 1 has the configuration as described above, mild plasma in comparison with the prior art may be generated easily and immediately, and the plasma jet may be generated and maintained stable without changing the shape and the length thereof. When the flow rate of the helium gas is 2 L/min and the power is on the order of 2 watts or so, a plasma jet having a diameter of approximately 1 mm and a length on the order of 20 mm or longer may be generated, so that the device is compact, light weight, easy-to-control, and superior in operability.

In order to confirm the medical effect of Example 1, a comatose mouse under isoflurane anesthesia was placed on an insulated table as an object to be treated and treatment was performed on the mouse by treating a femoral area where main artery was fractured and caused to bleed with the plasma jet of Example 1. Blood flowing out from the femoral main artery started hemostasis immediately after treatment to cover the bleeding site, whereby cessation of bleeding was achieved. Furthermore, from a histopathological point of view, tissue damage due to heat was not observed, and hence the effect of fine spot treatment of involved area was confirmed.

Other Examples of the present invention will be described below.

Example 2

Figure 3:
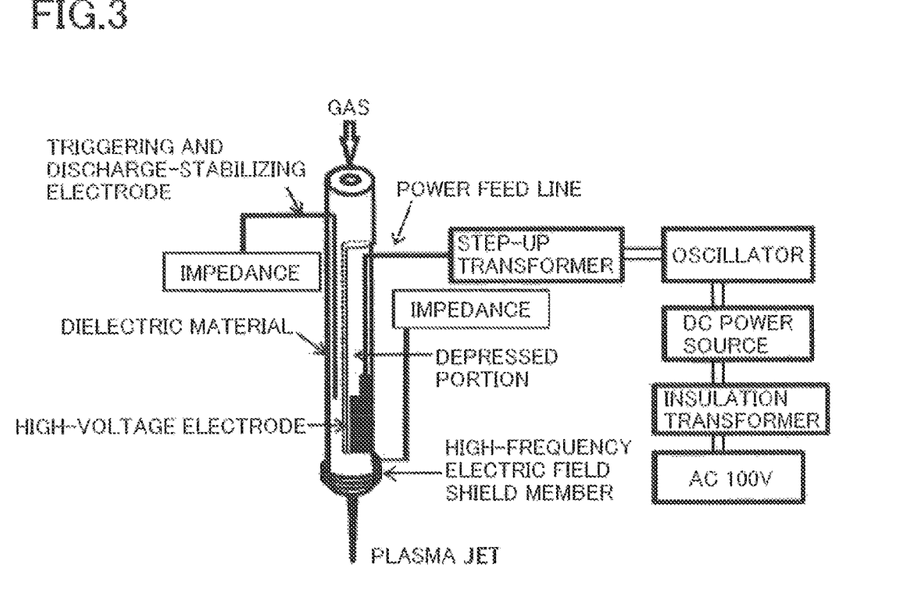
FIG. 3 is an explanatory drawing illustrating Example 2 of the present invention.

FIG. 3 is a plasma treatment equipment provided with a shield member for preventing leakage of high-frequency electric field on an outer surface of a dielectric material at a plasma ejection port of the plasma treatment equipment of the present invention described in FIG. 1 or FIG. 2. The shield member is let out to a space via impedance (earth capacity or the like) or grounded. Although the shield member is a copper wire coated with an insulating material such as vinyl in FIG. 3, a copper wire which is not coated is also applicable. The zero-potential side of the power source output may be grounded. In the medical application, the first priority is safety of human being as the object to be treated. Therefore, Example 2 is a configuration in which exposure to the high-frequency electric field is prevented, and a significant effect is expected for advanced control of excessive plasma treatment.

Example 3

Figure 4:
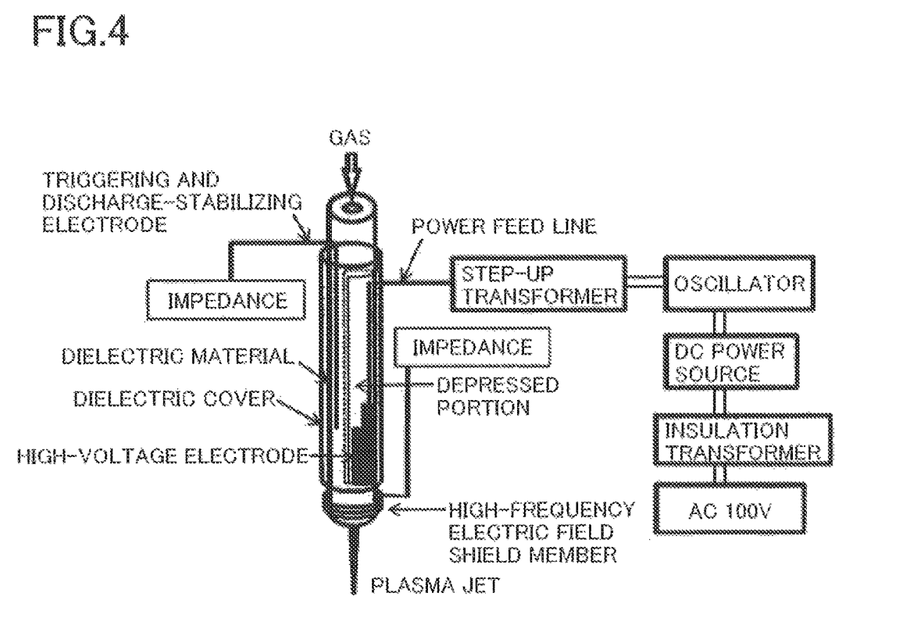
FIG. 4 is an explanatory drawing illustrating Example 3 of the present invention.

FIG. 4 is a plasma treatment equipment characterized in that the outside of the treatment device is covered with a dielectric cover as an insulating material in the plasma treatment equipment of the present invention illustrated in FIG. 1, FIG. 2, or FIG. 3. This Example has a configuration in which safety of the operator who executes the treatment is enhanced either in medical field or industrial field.

Example 4

Figure 5:
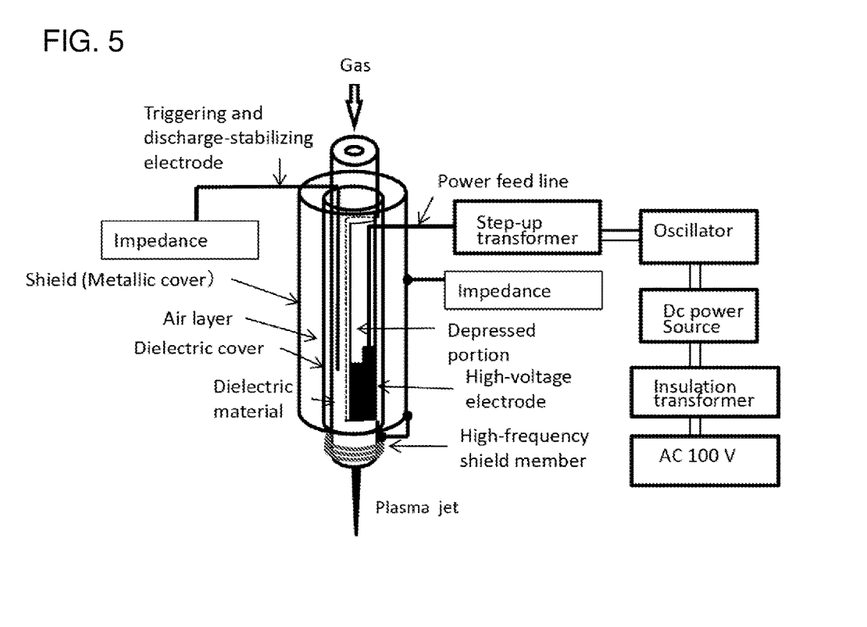
FIG. 5 is an explanatory drawing illustrating Example 4 of the present invention.

Example 4 has a configuration in which a high degree of safety is realized both for the object to be treated and the operator who executes the treatment. In other words, FIG. 5 illustrates the plasma treatment equipment of the present invention described in FIG. 1, FIG. 2, or FIG. 4, including a shield (metallic cover) covering the dielectric cover as the outside of the treatment equipment, an air layer provided between the dielectric cover and the metallic cover, which is the outside of the treatment equipment, and a high-frequency electric field shield member provided on the outer surface of the dielectric material as the plasma ejection port and electrically connected to the metallic cover in the vicinity of a tip end portion thereof, characterized in that the high-frequency electric field is hardly leaked and safety is enhanced. The metallic cover is connected to a zero-potential side of the power source output and may also be grounded. Also, in the plasma treatment equipment described above, the metallic cover may be covered with a sheet formed of an insulating material in order to further enhance the safety.

Since Examples 2 to 4 have the above-described configurations, respectively, plasma jet may be generated in the substantially same manner as Example 1.

(Example of Power Supply)

Figure 6:
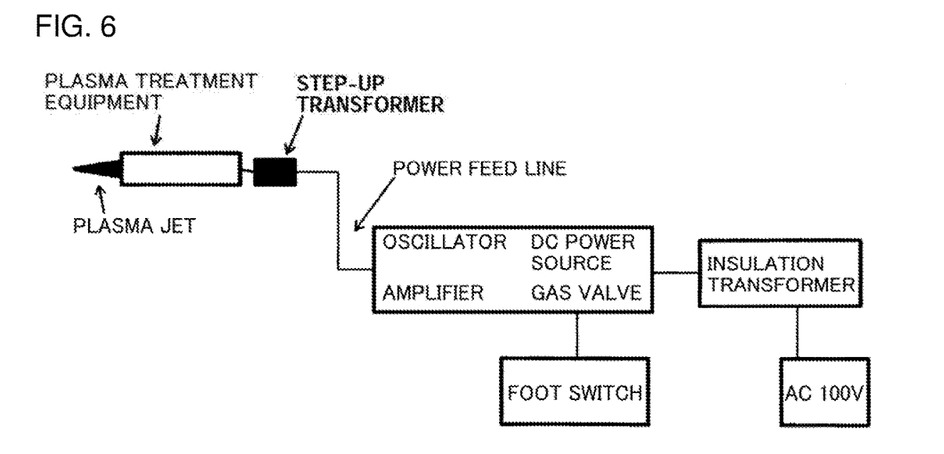
FIG. 6 is an explanatory drawing illustrating an example of a power supply of the present invention.

FIG. 6 illustrates a mode of the plasma treatment equipment of the present invention, configured to supply power to a piezoelectric element as a step-up power source by passing a voltage of 100 volts or so and having a frequency of approximately 1 to 1000 kHz through a power feed line on the order of several meters, and characterized in that ON and OFF of the power source and ON and OFF of a gas valve are controlled by using a foot switch or the like. The step-up power source may be a winding wire type step-up transformer instead of the piezoelectric element. Further, power may be supplied by providing an oscillator, an amplifier, a gas valve in the vicinity of the piezoelectric element and the plasma treatment equipment and passing a DC voltage on the order of 5 to 30 volts or so through the power feed line having a length on the order of several meters. Although the power is supplied from the commercial power source via the insulation transformer to the DC power source in the drawing, the DC power source may be replaced by a rechargeable battery. In FIG. 6, a pipe for supplying gas is not specifically illustrated. This mode may be configured not only as a hand-held type, but also as a type mounted on equipment such as a laparoscope, an endoscope, and the like.

INDUSTRIAL APPLICABILITY

The present invention is preferable for a hand-operable blood coagulation and hemostasis equipment, and may be applied as hemostasis equipment used at a laparoscopic surgery or endoscopic surgery. Further, the present invention may be used also in non-medical applications such as industrial applications in which various materials are subject to treatment with a plasma jet.

The invention claimed is:

1. Plasma treatment equipment, comprising:
a plasma starting and stabilizing unit comprising a single cylindrical dielectric material having an elongated hole for supplying gas connecting to a plasma ejection port, a triggering and discharge stabilizing electrode which comprises a wire or rod electrode embedded in a tube wall thickness portion of the dielectric material so as to extend along the longitudinal direction, and a high-voltage intense electric field electrode mounted on an outer surface of the dielectric material, the plasma starting and stabilizing unit being configured to start a plasma and to maintain a stable discharge of the plasma after starting of the plasma; and
a plasma generating unit, comprising the dielectric material having the elongated hole and a high-voltage plasma generating electrode located at the plasma ejection hole side relative to the high-voltage intense electric field electrode and having an area larger than that of the high-voltage intense electric field electrode, that is configured to perform main plasma generation in operation;
wherein the high-voltage intense electric field electrode is provided, as seen in a cross-sectional plane perpendicular to the axis of the elongated hole, so as to extend along the curvature of the dielectric material less than 180 degrees around the center of the elongated hole,
wherein the high-voltage plasma generating electrode is provided, as seen in the cross-sectional plane perpendicular to the axis, so as to extend along the curvature of the dielectric material to a greater extent than the high-voltage intense electric field electrode,
wherein the high-voltage intense electric field electrode is provided so as to face the triggering and discharge-stabilizing electrode across the elongated hole formed in the dielectric material,
wherein the triggering and discharge stabilizing electrode is not disposed to face the high-voltage plasma generating electrode across the elongated hole formed in the dielectric material; and
wherein the triggering and discharge stabilizing electrode, the high-voltage intense electric field electrode, and the high-voltage plasma generating electrode are provided in such a manner that the electrodes are not exposed but are covered with the dielectric material to the entire space of the elongated hole which allows passage of gas from an upper stream side, starting of the plasma, generation of the plasma, and ejection of a plasma jet.

2. The plasma treatment equipment of claim 1, wherein:
the high-voltage intense electric field electrode and the high-voltage plasma generating electrode are formed integrally and extending from an upstream direction of the gas toward the location of the plasma jet,
the integrally formed high-voltage intense electric field electrode and the high-voltage plasma generating electrode are provided in a depression formed on an outer circumference of the dielectric material and along a curvature of the dielectric material, and
the high-voltage intense electric field electrode is shorter than the high-voltage plasma generating electrode in the longitudinal direction.

3. The plasma treatment equipment of claim 1, wherein the triggering and discharge-stabilizing electrode and the high-voltage intense electric field electrode of the plasma starting and stabilizing unit are provided at positions so that electric field intensity is enhanced in the space in which gas passes discharge starts.

4. The plasma treatment equipment of claim 1, wherein a high-frequency electric field shield member formed of a metallic material and completely covered with an insulating material is provided on an outer surface of a tip end portion of the dielectric material, which constitutes the plasma ejection port, and wherein the metallic material is directly grounded or grounded by impedance.

5. The plasma treatment equipment of claim 1, wherein an inner surface of the elongated hole has concavities and convexities.

6. The plasma treatment equipment of claim 1, comprising a dielectric cover as an insulating material so as to cover the outer circumference of the dielectric material.

7. The plasma treatment equipment of claim 6, further comprising a metallic cover which covers the dielectric cover with an air layer in between.

8. The plasma treatment equipment of claim 7, further comprising a high-frequency electric field shield member formed of a metallic material completely covered with an insulating material and provided on an outer surface of a tip end portion of the dielectric material forming the plasma ejection port, wherein the high-frequency electric field shield member is electrically connected to the metallic cover in the vicinity of the tip end portion of the plasma ejection port, and wherein the metallic cover is connected to a zero potential side of a power source or grounded.

9. The plasma treatment equipment of claim 1, further comprising a high-voltage and high-frequency power source using a piezoelectric element.

10. The plasma treatment equipment of claim 1, further comprising a pulse gas supply device that is configured to supply gas to the elongated hole in a pulsed manner.

11. The plasma treatment equipment of claim 1, further comprising an ejector for a blood coagulation booster.

12. A plasma treatment method comprising treating an object with a plasma jet using the plasma treatment equipment of claim 1.

13. A plasma treatment method comprising treating an object with a blood coagulation booster or a material surface agent and treating the object with a plasma jet using the plasma treatment equipment of claim 1.

\* \* \* \* \*